United States Patent [19]

Crooker et al.

[11] Patent Number: 5,169,997
[45] Date of Patent: Dec. 8, 1992

[54] STABILIZED 1,1-DICHLORO-1-FLUOROETHANE

[75] Inventors: Richard M. Crooker, Lehigh; Maher Y. Elsheikh, Tredyffrin, both of Pa.

[73] Assignee: Elf Atochem North America, Inc., Philadelphia, Pa.

[21] Appl. No.: 774,026

[22] Filed: Oct. 9, 1991

[51] Int. Cl.$^5$ .......................... C07C 17/42; C07C 19/02
[52] U.S. Cl. ................................ 570/121; 252/182.24; 570/116; 570/118
[58] Field of Search ..................... 570/116, 121, 118

[56] References Cited

U.S. PATENT DOCUMENTS 2,364,588  12/1944  Morris et al. ...................... 570/116

FOREIGN PATENT DOCUMENTS 1056630  3/1989  Japan .................................. 570/116
1056631  3/1989  Japan .................................. 570/116

Primary Examiner—Joseph E. Evans

[57] ABSTRACT

HCFC blowing agents such as 141b which are stabilized with halogen-containing inhibitors such as benzyl bromide.

4 Claims, No Drawings

STABILIZED 1,1-DICHLORO-1-FLUOROETHANE

Field of the Invention

This invention relates to novel compositions of hydrochlorofluorocarbon ("HCFC") blowing agents such as 1,1-dichloro-1-fluoroethane ("141b") and stabilizing additives (or inhibitors) such as benzyl bromide, more particularly to compositions of HCFC blowing agents which are stabilized against decomposition in polyol premix formulations or the corresponding polyurethane or polyisocyanurate foams made therefrom.

BACKGROUND OF THE INVENTION

Polyurethane and polyisocyanurate foams are conventionally prepared by reacting an organic polyisocyanate (including diisocyanate) "A-side" component with a "B-side" polyol premix component containing organic polyol, blowing agent, surfactant, catalyst, and possibly other additives such as flame retardants, antioxidants, and U.V. stabilizers. These A-side and B-side components may be purchased by the end-user in separate containers and stored for later use. Since decomposition of the HCFC blowing agents has been observed in the B-side premixes during storage and during the process of making the foam, HCFC compositions inhibited against such decompositions would be highly desirable. For example, the preferred 141b blowing agent has been observed to decompose during the foam-making process to up to about 1%, depending on the formulation and reaction conditions, of various decomposition products of which by far the predominant product is 1-chloro-1-fluoroethylene ("1131a"). Inhibition of such decomposition is desired both because of toxicity concerns and because the decomposition is accompanied by the formation of equivalent amounts of acid which in turn causes catalyst deactivation.

Applicant is not aware of prior disclosures of the herein claimed formulations.

SUMMARY OF THE INVENTION

A composition is provided containing an HCFC blowing agent such as 141b and an inhibitor selected from t-butyl bromide or chloride, triphenylmethyl bromide or chloride, epibromohydrin, 4-methoxybenzyl chloride, or, preferably, benzyl bromide. When incorporated in a premix, the composition may also contain a polyol and, optionally, other ingredients such as surfactants, catalysts, and flame retardants.

DETAILED DESCRIPTION OF THE INVENTION

It has now been found that HCFC blowing agents such as 141b are stabilized against decomposition by the addition of one of aforementioned halogen-containing inhibitors such as benzyl bromide.

While the examples illustrate the invention with the preferred 141b blowing agent, the invention is also applicable to other HCFCs such as 2,2-dichloro-1,1,1-trifluoroethane ("123") and 2-chloro-1,1,1,2-tetrafluoroethane ("124").

The inhibitor is present in an effective amount, typically from about 0.01 to about 2% by weight, based on the weight of the blowing agent(s), preferably 0.05 to 1%.

The compositions may also include a polyol or a fully formulated B-side formulation containing polyol, catalyst, surfactant, and, optionally, other additives. Typical polyols are, for example, Stepanol PS 2502A, an aromatic polyester polyol sold by the Stepan Company; Terate 203, an aromatic polyester polyol sold by Hercules, Inc.; Pluracol Polyol 975, a sucrose-based polyol sold by BASF; Poly-G 71-530, a polyether polyol sold by Olin; and Quadrol, an amine-based polyol supplied by BASF. Typical catalysts include Potassium HEX-CEM, a potassium octoate sold by Mooney Chemicals; Polycat 41, an N,N,N-tri(dimethylaminopropyl)cyclohexatriazine catalyst sold by Air Products; Polycat 8, an N,N-dimethylcyclohexylamine catalyst sold by Air Products; Dabco TMR-30, a 2,4,6-tri(dimethylaminomethyl)phenol supplied by Air Products; and Dabco K-15, a potassium 2-ethylhexoate in diethylene glycol supplied by Air Products. A typical surfactant is Dow Corning 193, a silicone polymer surfactant. A typical A-side component is Mondur E-489, an aromatic diisocyanate supplied by Mobay Chemical Co., or Lupranate M20S, a polymethylenediisocyanate supplied by BASF.

The invention was illustrated by first preparing a polyurethane foam with 141b in the absence of inhibitor by stirring a formulation containing polyol (100 g of Stepanol PS 2502A), 141b (25.8 g), surfactant (1.51 g of Dow Corning 193), catalyst (2.82 g of Potassium HEX-CEM and 0.7 g of Polycat 41), and diisocyanate (127.2 g of Mondur E-489). The contents were poured into a box and the resulting foam was left to cool to room temperature. After curing the foam at 250° F. for 20 hours, the cell gas was analyzed by crushing a sample and injecting the released gas mixture directly to a gas chromatograph. The gas was found to contain 2180 ppm of 1131a, whereas the 141b starting material contained only 10 ppm of 1131a. Other minor components in the cell gas totalled only about 440 ppm, similar to the levels found in the 141b starting material. When 0.6 weight % of each of benzyl bromide, t-butyl chloride, and epibromohydrin were dissolved in 141b, foams prepared as aforesaid contained only 1077 ppm, 1154 ppm, and 1195 ppm of 1131a, respectively.

In another illustration, a polyurethane foam was prepared with 141b in the absence of inhibitor by stirring a B-side formulation containing polyol (60 g of Pluracol Polyol 975 and 40 g of Quadrol), 141b (30 g), surfactant (1.5 g of Dow Corning 193), and catalyst (2.5 g of Polycat 8) with an A-side comprised of diisocyanate (118.7 g of Lupranate M20S). The resulting foam was cured at 121 degrees Centigrade and analyzed as in the first illustration. The cell gas was found to contain 2313 ppm of 1131a. When 0.6 weight % of each of t-butyl bromide, triphenylmethyl chloride, triphenylmethyl bromide, and 4-methoxybenzyl chloride was dissolved in the 141b, foam prepared as aforesaid contained only 1443 ppm, 1450 ppm, 1343 ppm, and 1125 ppm of 1131a, respectively.

In a third test, polyisocyanurate premixes containing 141b (uninhibited and inhibited with 0.6 weight % of each of benzyl bromide and epibromohydrin) were aged at 130 degrees F. The premixes contained a polyol (100 g of Stepanol PS-2502A), 141b (37 g), surfactant (3 g of Dow Corning 193), and catalyst (2.8 g of Dabco K-15 and 0.9 g of Dabco TMR-30). The uninhibited premix was found to contain 100 ppm of 1131a, while the premix containing the preferred benzyl bromide inhibitor contained only 40 ppm of 1131a. Epibrombhydrin was not effective in this test, the aged premix being found to contain 270 ppm of 1131a.

What is claimed is:

1. A composition comprising 1,1-dichloro-1fluoroethane and an inhibitor selected from benzyl bromide, t-butyl chloride, t-butyl bromide, epibromohydrin, triphenylmethyl chloride, triphenylmethyl bromide, or 4-methoxybenzyl chloride.

2. A composition as in claim 1 wherein the inhibitor is benzyl bromide.

3. A composition containing a hydrochlorofluorocarbon blowing agent and an inhibitor selected from benzyl bromide, t-butyl chloride, t-butyl bromide, epibromohydrin, triphenylmethyl chloride, triphenylmethyl bromide, or 4-methoxybenzyl chloride.

4. A composition as in claim 3 wherein the hydrochlorofluoro carbon blowing agent is selected from 2,2-dichloro-1,1,1-trifluoroethane ("123") and 2-chloro-1,1,1,2-tetrafluoroethane ("124").

* * * * *